United States Patent
He et al.

(10) Patent No.: US 12,117,385 B1
(45) Date of Patent: Oct. 15, 2024

(54) METHOD FOR EVALUATING THE UNDERGROUND HYDROGEN STORAGE (UHS) CAPACITY IN POROUS MEDIA OF DEPLETED GAS RESERVOIRS USING $CO_2$ AS CUSHION GAS

(71) Applicant: Southwest Petroleum University, Chengdu (CN)

(72) Inventors: Youwei He, Chengdu (CN); Yu Qiao, Chengdu (CN); Jiazheng Qin, Chengdu (CN); Yong Tang, Chengdu (CN); Ning Wang, Chengdu (CN); Guoqing Zhao, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 18/314,395

(22) Filed: May 9, 2023

(30) Foreign Application Priority Data

Mar. 21, 2023 (CN) .......................... 202310281755.2

(51) Int. Cl.
  *G01N 15/08* (2006.01)
  *E21B 49/00* (2006.01)
  *G01N 33/24* (2006.01)

(52) U.S. Cl.
  CPC ........... *G01N 15/088* (2013.01); *E21B 49/00* (2013.01); *G01N 33/24* (2013.01); *E21B 2200/20* (2020.05)

(58) Field of Classification Search
  CPC ....... G01N 15/088; G01N 33/24; E21B 49/00
  See application file for complete search history.

(56) References Cited

U.S. PATENT DOCUMENTS 9,718,618 B2 * 8/2017 Oates ................... B01D 53/265
2012/0065951 A1 3/2012 Roy et al.
(Continued)

FOREIGN PATENT DOCUMENTS

CN 106902723 A 6/2017
CN 111649237 A 9/2020
(Continued)

OTHER PUBLICATIONS

AL homoud et al. Investigation on the Impact of Cushion Gases in Saline Aquifer: Implication for Underground H2 Storage, SPE-218921-MS (Year: 2024).*
(Continued)

*Primary Examiner* — John Fitzgerald
(74) *Attorney, Agent, or Firm* — Nitin Kaushik

(57) ABSTRACT

Disclosed is a method for evaluating the underground hydrogen storage (UHS) capacity in porous media of depleted gas reservoirs using $CO_2$ as cushion gas, including the following steps: S1: obtaining physical parameters required for UHS capacity evaluation based on geological and production data of the target depleted gas reservoir; S2: calculating the cap-rock breakthrough pressure and fault-slip pressure of the UHS based on the cap and fault properties of the target depleted gas reservoir to further estimate the highest operating pressure of the UHS; S3: developing the $H_2$—$CO_2$—$CH_4$ multi-component material balance equation in underground porous media by considering the dissolution of three components in formation water; S4: substituting the parameters obtained from S1 and S2 into the multi-component material balance equation to calculate the proportion of different gas components in the pore space to finally determine the UHS capacity of the target depleted gas reservoir.

8 Claims, 5 Drawing Sheets

(56) References Cited

U.S. PATENT DOCUMENTS

2016/0060038 A1* 3/2016 Oates .................. B01D 53/265
                                                        62/515
2022/0099519 A1* 3/2022 Shi ........................ G01M 3/26

FOREIGN PATENT DOCUMENTS

| CN | 216449569 U | | 5/2022 | |
|---|---|---|---|---|
| CN | 115034489 A | | 9/2022 | |
| CN | 115078214 A | * | 9/2022 | ........... G01N 15/088 |
| CN | 115270536 A | | 11/2022 | |
| CN | 115758936 A | | 3/2023 | |

OTHER PUBLICATIONS

Alholan et al. "Advancing Hydrogen Storage in Depleted Gas Reservoirs: A Comprehensive Evaluation of Dominant Trapping Mechanisms" IPTC-24019-MS (Year: 2024).*

Amiri et al. "Investigation of Synergy Between Extended Oil Recovery and Hydrogen Storage in a Producing Field Using Norne Reservoir Model" Society of Petroleum Engineers SPE-218453-MS (Year: 2024).*

* cited by examiner

METHOD FOR EVALUATING THE UNDERGROUND HYDROGEN STORAGE (UHS) CAPACITY IN POROUS MEDIA OF DEPLETED GAS RESERVOIRS USING $CO_2$ AS CUSHION GAS

CROSS-REFERENCE TO RELATED APPLICATIONS

The application claims priority to Chinese patent application No. 2023102817552, filed on Mar. 21, 2023, the entire contents of which are incorporated herein by reference.

TECHNICAL FIELD

The present invention relates to the technical field of oil and gas field development, hydrogen energy and energy storage, in particular to a method for evaluating the underground hydrogen storage (UHS) capacity in porous media of depleted gas reservoirs using $CO_2$ as cushion gas.

BACKGROUND

The hydrogen energy is a renewable, high-energy and high-efficiency energy carrier, which is convenient for storage and conversion. China's solar power and wind power industry is large in scale, but these two types of power utilization are low, and the waste electricity cannot be utilized, so the hydrogen energy becomes a favorable energy conversion carrier. The hydrogen energy is widely used in steel, chemical and petrochemical industries, replacing fossil energy such as coal and oil. It is expected that the demand for hydrogen energy in the industrial field will exceed 35 million tons in 2050, and the demand is huge. Along with the implementation of the "carbon neutrality, carbon emissions peak" policy, the hydrogen energy will play an important role as a clean energy source.

The hydrogen energy storage is mainly divided into the physical hydrogen storage and the chemical hydrogen storage. The physical hydrogen storage mainly includes high-pressure gaseous hydrogen storage, low-temperature liquid hydrogen storage, activated carbon adsorption hydrogen storage, carbon fiber and carbon nanotube hydrogen storage, and underground hydrogen storage. The chemical hydrogen storage mainly includes metal hydride hydrogen storage, liquid organic hydrogen carrier hydrogen storage, inorganic hydrogen storage, and liquid ammonia hydrogen storage. The UHS is an effective way of large-capacity and long-term energy storage. Similar to underground gas storage, natural gas is often stored in depleted oil and gas reservoirs, aquifers, salt caverns and some abandoned pit caverns. There are higher requirements for underground storage of hydrogen, and the focus of the UHS research is to store hydrogen in depleted gas reservoirs and salt caverns. The UHS in depleted gas reservoir has the advantages of large volume, high geological awareness, good sealing and wide geographical distribution; the depleted gas reservoir usually contains a certain volume of residual gas, which can be used as cushion gas; meanwhile, the underground and surface original facilities can be partially utilized to reduce the investment cost of the UHS construction.

The development of UHS technology is an effective way to overcome the volatility and intermittency of renewable energy. The hydrogen storage capacity is a key factor for design engineers to consider and is an important indicator of the performance of the UHS. It is important to account for the volume of hydrogen stored in the UHS in real time and to determine the working gas volume at different pressures. Depleted gas reservoirs are the most common and economical form of building the UHS. Replacing valuable primary cushion gas with cheap $CO_2$ not only reduces the loss of hydrogen but also achieves the purpose of carbon storage. The construction of UHS with $CO_2$ as cushion gas not only achieves carbon emission reduction, but also improves the utilization of low-carbon energy. Compared with the primary cushion gas and $N_2$, $CO_2$ has stronger compressibility, which can improve the $CO_2$ storage capacity of depleted gas reservoirs and enhance the hydrogen recovery efficiency in the process of hydrogen extraction. However, the existing UHS capacity evaluation method cannot accurately evaluate the hydrogen storage capacity in porous media of depleted gas reservoirs using $CO_2$ as cushion gas. When $CO_2$ is used as the cushion gas of the UHS of the depleted gas reservoir, it needs to consider the equilibrium relationship of $H_2$—$CO_2$—$CH_4$ multi-component so that the hydrogen storage capacity of this reservoir can be evaluated more accurately.

SUMMARY

In response to the above problems, the present invention aims to provide a method for evaluating the underground hydrogen storage (UHS) capacity in porous media of depleted gas reservoirs using $CO_2$ as cushion gas.

The technical solution of the present invention is as follows:

A method for evaluating the UHS capacity in porous media of depleted gas reservoirs using $CO_2$ as cushion gas, comprising the following steps:

S1: obtaining physical parameters required for hydrogen storage capacity evaluation based on geological and production data of the target depleted gas reservoir;

S2: calculating the cap-rock breakthrough pressure and fault-slip pressure of the UHS based on the cap and fault properties of the target depleted gas reservoir to further estimate the highest operating pressure of the UHS;

S3: developing the $H_2$—$CO_2$—$CH_4$ multi-component material balance equation in underground porous media by considering the dissolution of three components of hydrogen, carbon dioxide and methane in formation water, and using the molar weight material balance method, and simulating the UHS injection with a high pressure and high temperature device to verify the accuracy of the $H_2$—$CO_2$—$CH_4$ multi-component material balance equation;

S4: substituting the parameters obtained from S1 and S2 into the $H_2$—$CO_2$—$CH_4$ multi-component material balance equation to calculate the proportion of different gas components in the pore space to finally determine the UHS capacity of the target depleted gas reservoir.

Preferably, in S1, the physical parameters include original geological reserves, water saturation, water body size, temperature of the depleted gas reservoir, pressure of the depleted gas reservoir, formation water intrusion under depleted formation conditions, accumulated water production, gas component, formation water mineralization.

Preferably, in S2, the cap-rock breakthrough pressure is calculated by the following equation:

$$\chi = 1 - \frac{(\sigma_1 - \sigma_3)/2}{c\cos\phi + (\sigma_1 + \sigma_3)\sin\phi/2} = 1 - \frac{\tau_m}{\tau_m^*} \tag{1}$$

where, $\chi$ is the cap safety factor; when $\chi=0$, the shear failure occurs; $\sigma_1$ is the maximum effective principal stress, MPa; $\sigma_3$ is the minimum effective principal stress, MPa; c is the cohesion force, MPa; $\phi$ is the internal friction angle, °; $\tau_m$ is the maximum shear stress at a certain stress state, MPa; $\tau_m^*$ is the critical shear stress when the shear failure occurs, MPa.

Preferably, in S2, the fault-slip pressure is calculated by the following equation:

$$ST = \frac{\tau_s}{\sigma_n} \quad (2)$$

$$\sigma = \frac{\sigma_H + \sigma_h}{2} + \frac{\sigma_H - \sigma_h}{2}\cos 2\alpha \quad (3)$$

$$\tau = \frac{\sigma_H - \sigma_h}{2}\sin 2\alpha \quad (4)$$

where, ST is the fault slip trend index; when ST<0.6, the fault is mechanically stable; when ST≥0.6, the fault is at risk of slip; the larger the ST, the higher the risk of slip; $\tau$ and $\tau_s$ are the fault shear stress and the shear stress along the fault plane under a certain stress state respectively, MPa; $\sigma$ and $\sigma_n$ are the positive stress perpendicular to the fault plane and the effective positive stress respectively, MPa; $\sigma_n$ and $\sigma_h$ are the maximum principal stress and the minimum principal stress respectively, MPa; $\alpha$ is the dip angle of the fault plane, °.

Preferably, in S2, the highest operating pressure of the UHS is determined. The cap-rock breakthrough pressure and the fault-slip pressure are compared, and the smaller one is the highest operating pressure of the UHS.

Preferably, in S3, the $H_2$—$CO_2$—$CH_4$ multi-component material balance equation is:

$$\frac{p_{sc}V_{CO2\_inj}}{Z_{sc}RT_{sc}} = \frac{pV_{CO_2}}{Z_{CO_2}RT} + \frac{p_{sc}V_{CO2\_dis}}{Z_{sc}RT_{sc}} \quad (5)$$

$$\frac{p_{dep}V_{H\_dep}}{Z_{H\_dep}RT_{dep}} + \frac{p_{sc}V_{dep\_dis}}{Z_{sc}RT_{sc}} = \frac{pV_H}{Z_H RT} + \frac{p_{sc}V_{H\_dis}}{Z_{sc}RT_{sc}} \quad (6)$$

$$\frac{p_{sc}V_{H2\_inj}}{Z_{sc}RT_{sc}} = \frac{pV_{H_2}}{Z_{H_2}RT} + \frac{p_{sc}V_{H2\_dis}}{Z_{sc}RT_{sc}} \quad (7)$$

where, $p_{sc}$, p and $p_{dep}$ are the standard condition pressure, formation pressure, pressure of the depleted gas reservoir, respectively. MPa; $V_{CO2\_inj}$, $V_{CO2}$ and $V_{CO2\_dis}$ is are the volume of injected $CO_2$, the volume of $CO_2$ in the formation, and the volume of dissolved $CO_2$, respectively, m³; $Z_{sc}$, $Z_{CO2}$, $Z_{H\_dep}$, $Z_H$ and $Z_{H2}$ are the gas deviation factor under standard conditions, $CO_2$ deviation factor, natural gas deviation factor under depleted formation conditions, natural gas deviation factor under formation conditions, and $H_2$ deviation factor, respectively, R is the ideal gas constant, 0.00831451 J·mol⁻¹·k⁻¹; $T_{sc}$, T and $T_{dep}$, are the standard condition temperature, formation temperature, and temperature of the depleted gas reservoir, respectively, K; $V_{H\_dep}$, $V_{dep\_dis}$, $V_H$ and $V_{H\_dis}$ are the volume of natural gas in the depleted gas reservoir formation, the volume of natural gas dissolved in the depleted gas reservoir formation, the volume of natural gas in the gas reservoir formation, and the volume of natural gas dissolved in the formation, respectively, m³; $V_{H2\_inj}$, $V_{H2}$ and $V_{H2\_dis}$ are the volume of injected $H_2$, the volume of $H_2$ in the formation pore, and the volume of dissolved $H_2$ in the formation, respectively, m³.

Preferably, in S4, the proportion of different gas components in the reservoir pore space is calculated. The proportion of $CO_2$ in the reservoir pore space is calculated by substituting the following equation into the $H_2$—$CO_2$—$CH_4$ multi-component material balance equation:

$$V_{CO_2} = aV \quad (8)$$

$$V = V_i[1 - c_{eff}(p_i - p)] + V_{w\_p}B_w - W_e \quad (9)$$

$$V_i = G_i B_i = G_i\left(\frac{p_{sc}}{Z_{sc}/T_{sc}}\right)\Big/\left(\frac{p_i}{Z_i/T_i}\right) \quad (10)$$

$$V_{CO2\_dis} = \left[\frac{V_i(S_w + M)}{(1-S_w)B_{wi}} - V_{w\_p} - \frac{aVS_w}{(1-S_w)B_w}\right]R_{CO2} \quad (11)$$

Where, a is the proportion of $CO_2$ occupying the gas-bearing pore space of the formation excluding the water intrusion volume; V and $V_i$ are the gas-bearing pore space in the formation under different pressure conditions and the gas-bearing pore space in the formation under initial conditions, respectively, m³; $c_{eff}$ is the effective compression coefficient of the formation, MPa⁻¹; $p_i$ is the initial formation pressure, MPa; $V_{w\_p}$ is the water production volume, m³; $B_w$ and $B_{wi}$ are the formation water volume coefficient and the initial formation water volume coefficient, respectively; $W_e$ is the water intrusion volume, m³; $G_i$ is the gas reservoir reserve, m; $B_i$ is natural gas volume coefficient under initial formation conditions; $Z_i$ is the initial formation natural gas deviation factor; $T_i$ is the initial formation temperature, K; $S_w$ is the water saturation; M is the water body multiplier; $R_{CO2}$ is the $CO_2$ solubility in formation water, m³/m³.

Preferably, in S4, the proportion of different gas components in the reservoir pore space is calculated, the proportion of $CH_4$ in the reservoir pore space is calculated by substituting the following equation into the $H_2$—$CO_2$—$CH_4$ multi-component material balance equation:

$$V_H = bV \quad (12)$$

$$V_{H\_dis} = \left[\frac{bVS_w}{(1-S_w)B_w}\right]R_H \quad (13)$$

$$V_{dep} = V_i[1 - c_{eff}(p_i - p_{dep})] + V_{w\_p}B_{w\_dep} - W_{e\_dep} \quad (14)$$

$$V_{dep\_dis} = \left[\frac{V_i(S_w + M)}{(1-S_w)B_{wi}} - V_{w\_p}\right]R_{H\_dep} \quad (15)$$

Where, b is the proportion of natural gas occupying the gas-bearing pore space excluding the water intrusion volume; $V_{dep}$ is the gas-bearing pore space in the formation under depleted formation conditions, m³, $B_{w\_dep}$ is the formation water volume coefficient in the depleted formation condition; $W_{e\_dep}$ is the water intrusion volume in the depleted formation condition, m³; $R_H$ and $R_{H\_dep}$ are the solubility of natural gas under formation conditions and the solubility of natural gas under depleted formation conditions.

Preferably, in S4, the proportion of different gas components in the reservoir pore space is calculated, the proportion of $H_2$ in the reservoir pore space is calculated by substituting the following equation into the $H_2$—$CO_2$—$CH_4$ multi-component material balance equation:

$$V_{H_2} = (1-a-b)V \quad (16)$$

$$V_{H_2\_dis} = \left[\frac{(1-a-b)VS_w}{(1-S_w)B_w}\right]R_{H_2} \quad (17)$$

Where, $R_{H_2}$ is the solubility of $H_2$ under formation conditions, $m^3/m^3$;

The calculated $V_{H_2\_inj}$ value is the UHS capacity of the target depleted gas reservoir.

Preferably, the high pressure and high temperature device comprises an injection device, a core device, a back-pressure device I, a back-pressure device II, and a vacuum extraction device.

The injection device comprises a gas cylinder, a compressor, a gas intermediate vessel and a pressure pump I connected in sequence. The gas intermediate vessel is further connected to the input end of the core device. The gas cylinder comprises an $H_2$ gas cylinder, a $CO_2$ gas cylinder and a $CH_4$ gas cylinder arranged in parallel, and the gas intermediate vessel comprises an $H_2$ intermediate vessel, a $CO_2$ intermediate vessel and a $CH_4$ intermediate vessel.

The core device comprises a core holder arranged in an oven, a confining pressure pump and a formation water intermediate vessel. The back-pressure device I comprises a pressure pump II and a back-pressure valve I. The core holder is provided with a pressure gauge I and a pressure gauge II respectively at the left and right ends. The confining pressure pump is connected to the core holder. The output end of the core holder is connected to the formation water intermediate vessel, and the other end of the formation water intermediate vessel is connected to the pressure pump II. The pressure pump II is connected to the output end of the core holder via the back-pressure valve I.

The back-pressure device II comprises a pressure pump III and a back-pressure valve II, and the other end of the back-pressure valve II is connected to the input end of the core holder;

The vacuum extraction device comprises an evacuator and a pressure gauge III. The evacuator is connected to the input end of the core holder, and the pressure gauge III is provided on the connected line.

A valve is provided between sub-components, and a one-way valve for flowing from the gas cylinder to the gas intermediate vessel is further provided between the $H_2$ gas cylinder and the $H_2$ intermediate vessel, between the $CO_2$ gas cylinder and the $CO_2$ intermediate vessel, and between the $CH_4$ gas cylinder and the $CH_4$ intermediate vessel.

The present invention has the following beneficial effects:

The method of evaluating hydrogen storage capacity described in the present invention takes into account the effect of $CO_2$ as cushion gas on the UHS capacity in porous media of depleted gas reservoirs, which can evaluate the UHS capacity more accurately and provide technical support for the design and operation of the UHS.

BRIEF DESCRIPTION OF DRAWINGS

In order to explain the embodiments of the present invention or the technical solutions in the prior art more clearly, the following will make a brief introduction to the drawings needed in the description of the embodiments or the prior art. Obviously, the drawings in the following description are merely some embodiments of the present invention. For those of ordinary skill in the art, other drawings can be obtained based on the structures shown in these drawings without any creative effort.

Explanation of numbers marked in the figure.

1—$H_2$ gas cylinder, 2—$CO_2$ gas cylinder, 3—$CH_4$ gas cylinder, 4—Pressure pump 1, 5—Four-way valve I, 6—Valve I, 7—Valve II, 8—Valve II, 9—Valve IV, 10—Valve V, 11—Valve VI, 12—$H_2$ intermediate vessel. 13—$CO_2$ intermediate vessel, 14—$CH_4$ intermediate vessel, 15—Valve VII, 16—Valve VIII, 17—Valve IX, 18—Compressor, 19—One-way valve I, 20—One-way valve II, 21—Four-way valve II, 22—Valve X, 23—One-way valve III, 24—Vacuum extractor, 25—Pressure gauge III, 26—Valve XI, 27—Four-way valve III, 28—Valve XII, 29—Oven. 30—Three-way valve, 31—Pressure gauge I, 32—Confining pressure pump, 33—Core holder, 34—Outcrop core, 35—Four-way valve IV, 36—Pressure gauge II, 37—Valve XIII, 38—Back-pressure valve I, 39—Valve XIV, 40—Valve XV, 41—Formation water intermediate vessel, 42—Valve XVI, 43—Pressure pump II, 44—Valve XVII, 45—Back-pressure valve II, 46—Pressure pump III.

DETAILED DESCRIPTION OF THE EMBODIMENTS

The present invention is further described with reference to the drawings and embodiments. It should be noted that the embodiments in this application and the technical features in the embodiments can be combined with each other without conflict. It is to be noted that, unless otherwise specified, all technical and scientific terms herein have the same meaning as commonly understood by those of ordinary skill in the art to which this application belongs. "Include" or "comprise" and other similar words used in the present disclosure mean that the components or objects before the word cover the components or objects listed after the word and its equivalents, but do not exclude other components or objects.

Figure 1:
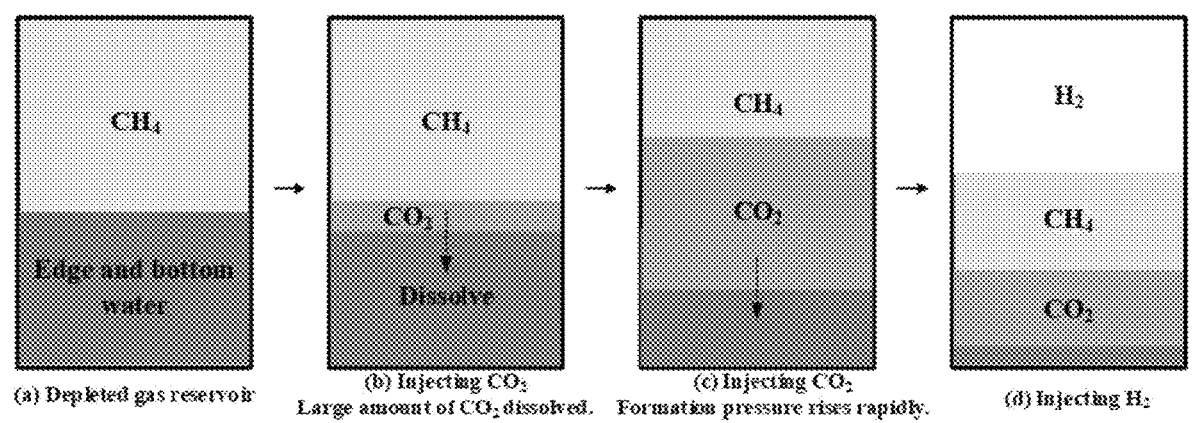
FIG. 1 shows the stage of injection about $CO_2$ as cushion gas and $H_2$ gas in the porous media of depleted gas reservoir.
Figure 2:
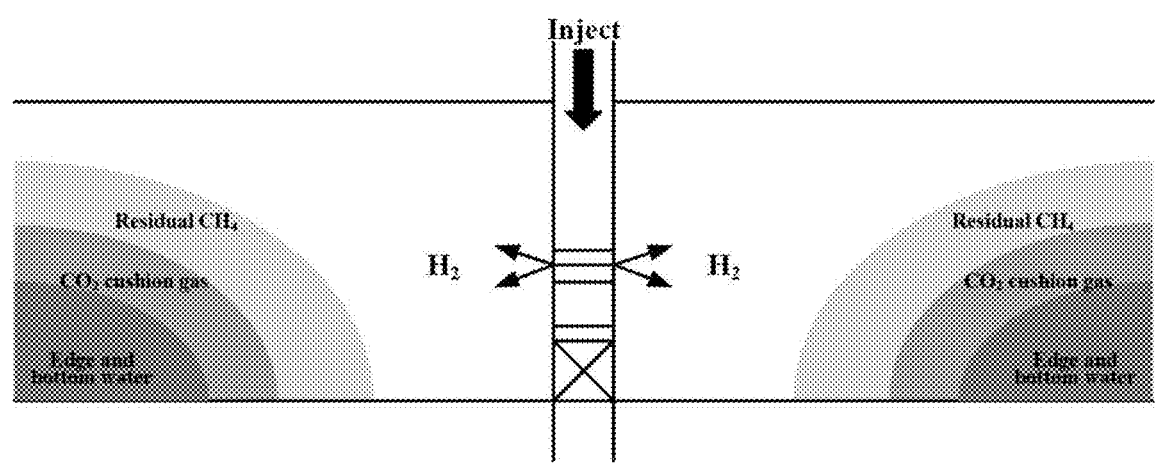
FIG. 2 shows a schematic diagram of the distribution of gas components during the injection process.

As shown in FIGS. 1-2, the present invention provides a method for evaluating the UHS capacity in porous media of depleted gas reservoirs using $CO_2$ as cushion gas, comprising the following steps of:

S1: obtaining physical parameters required for hydrogen storage capacity evaluation based on geological and production data of the target depleted gas reservoir.

In a specific embodiment, the physical parameters include original geological reserves, water saturation, water body size, temperature of depleted gas reservoir, pressure of depleted gas reservoir, formation water intrusion under depleted formation conditions, accumulated water production, gas component, formation water mineralization.

S2: calculating the cap-rock breakthrough pressure and fault-slip pressure of the UHS based on the cap and fault properties of the target depleted gas reservoir to further estimate the highest operating pressure of the UHS. The highest operating pressure of the UHS is determined. The cap-rock breakthrough pressure and the fault-slip pressure are compared, and the smaller one is the highest operating pressure of the UHS.

In a specific embodiment, the cap-rock breakthrough pressure is calculated by the following equation:

$$\chi = 1 - \frac{(\sigma_1 - \sigma_3)/2}{c\cos\phi + (\sigma_1 + \sigma_3)\sin\phi/2} = 1 - \frac{\tau_m}{\tau_m^*} \quad (1)$$

where, $\chi$ is the cap safety factor; when $\chi=0$, the shear failure occurs, $\sigma_1$ is the maximum effective principal stress (the difference between the maximum principal stress $\sigma_H$ and the formation pressure), MPa; $\sigma_3$ is the minimum effective principal stress (the difference between the minimum principal stress $\sigma_h$ and the formation pressure), MPa; c is the cohesion force, MPa; $\phi$ is the internal friction angle, °; $\tau_m$ is the maximum shear stress at a certain stress state, MPa; $\tau_m^*$ is the critical shear stress when the shear failure occurs, MPa.

The fault-slip pressure is calculated by the following equation:

$$ST = \frac{\tau_s}{\sigma_n} \quad (2)$$

$$\sigma = \frac{\sigma_H + \sigma_h}{2} + \frac{\sigma_H - \sigma_h}{2}\cos 2\alpha \quad (3)$$

$$\tau = \frac{\sigma_H - \sigma_h}{2}\sin 2\alpha \quad (4)$$

where, ST is the fault slip trend index; when ST<0.6, the fault is mechanically stable; when ST≥0.6, the fault is at risk of slip; the larger the ST, the higher the risk of slip; $\tau$ and $\tau_s$ are the fault shear stress and the shear stress along the fault plane under a certain stress state respectively, MPa; $\sigma$ and $\sigma_n$ are the positive stress perpendicular to the fault plane and the effective positive stress respectively, MPa; $\sigma_H$ and $\sigma_h$ are the maximum principal stress and the minimum principal stress respectively, MPa; $\alpha$ is the dip angle of the fault plane, °.

It should be noted that the formula for calculating the cap-rock breakthrough pressure and fault-slip pressure in the above embodiment is only the preferred calculation method of the present invention, which can obtain a more accurate the highest pressure of the formation. Other calculation methods for considering this corresponding parameter can also be applied to the present invention. For example, the cap-rock breakthrough pressure can be determined using shear dilatancy safety factor, tensile damage limit pressure, uniaxial tensile strength, etc. And the fault-slip pressure can be determined using fault activation enabling limit pressure, fault-slip limit pressure, and fault closure factor.

S3: developing the $H_2$—$CO_2$—$CH_4$ multi-component material balance equation in underground porous media by considering the dissolution of three components of hydrogen, carbon dioxide and methane in formation water, and using the molar weight material balance method.

In a specific embodiment, the Hz-$CO_2$—$CH_4$ multi-component material balance equation is:

$$\frac{p_{sc}V_{CO_2\_inj}}{Z_{sc}RT_{sc}} = \frac{pV_{CO_2}}{Z_{CO_2}RT} + \frac{p_{sc}V_{CO_2\_dis}}{Z_{sc}RT_{sc}} \quad (5)$$

$$\frac{p_{dep}V_{H\_dep}}{Z_{H\_dep}RT_{dep}} + \frac{p_{sc}V_{dep\_dis}}{Z_{sc}RT_{sc}} = \frac{pV_H}{Z_HRT} + \frac{p_{sc}V_{H\_dis}}{Z_{sc}RT_{sc}} \quad (6)$$

$$\frac{p_{sc}V_{H_2\_inj}}{Z_{sc}RT_{sc}} = \frac{pV_{H_2}}{Z_{H_2}RT} + \frac{p_{sc}V_{H_2\_dis}}{Z_{sc}RT_{sc}} \quad (7)$$

where, $p_{sc}$, p and $p_{dep}$ are the standard condition pressure, formation pressure, and pressure of the depleted gas reservoir, respectively, MPa; $V_{CO_2\_inj}$, $V_{CO_2}$ and $V_{CO_2\_dis}$ are the volume of injected $CO_2$, the volume of $CO_2$ in the formation, and the volume of dissolved $CO_2$, respectively, m³; $Z_{sc}$, $Z_{CO_2}$, $Z_{H\_dep}$, $Z_H$ and $Z_{H2}$ are the gas deviation factor under standard conditions. $CO_2$ deviation factor, natural gas deviation factor under depleted formation conditions, natural gas deviation factor under formation conditions, and $H_2$ deviation factor, respectively; R is the ideal gas constant, 0.00831451 J·mol⁻¹·k⁻¹; $T_{sc}$, T and $T_{dep}$, are the standard condition temperature, formation temperature, and temperature of the depleted gas reservoir, respectively. K; $V_{H\_dep}$, $V_{dep\_dis}$, $V_H$ and $V_{H\_dis}$ are the volume of natural gas in the depleted gas reservoir formation, the volume of natural gas dissolved in the depleted gas reservoir formation, the volume of natural gas in the gas reservoir formation, and the volume of natural gas dissolved in the formation, respectively, m³; $V_{H2\_inj}$, $V_{H2}$ and $V_{H2\_dis}$ are the volume of injected $H_2$, the volume of $H_2$ in the formation pore, and the volume of dissolved $H_2$ in the formation, respectively, m³.

S4: substituting the parameters obtained from S1 and S2 into the $H_2$—$CO_2$—$CH_4$ multi-component material balance equation to calculate the proportion of different gas components in the pore space to finally determine the UHS capacity of the target depleted gas reservoir.

In a specific embodiment, when the proportion of different gas components in the reservoir pore space is calculated, the proportion of $CO_2$ in the reservoir pore space is calculated by substituting the following equation into the $H_2$—$CO_2$—$CH_4$ multi-component material balance equation:

$$V_{CO_2} = aV \quad (8)$$

$$V = V_i[1 - c_{eff}(p_i - p)] + V_{w\_p}B_w - W_e \quad (9)$$

$$V_i = G_iB_i = G_i\left(\frac{p_{sc}}{Z_{sc}/T_{sc}}\right)\bigg/\left(\frac{p_i}{Z_i/T_i}\right) \quad (10)$$

$$V_{CO_2\_dis} = \left[\frac{V_i(S_w + M)}{(1 - S_w)B_{wi}} - V_{w\_p} - \frac{aVS_w}{(1 - S_w)B_w}\right]R_{CO_2} \quad (11)$$

where, a is the proportion of $CO_2$ occupying the gas-bearing pore space of the formation excluding the water intrusion volume; V and $V_i$ are the gas-bearing pore space in the formation under different pressure conditions and the gas-bearing pore space in the formation under initial conditions, respectively, m³; $c_{eff}$ is the effective compression coefficient of the formation, MPa⁻¹; $p_i$ is the initial formation pressure, MPa; $V_{w\_p}$, is the water production volume, m³; $B_w$ and $B_{wi}$ are the formation water volume coefficient and the initial formation water volume coefficient, respectively; $W_e$ is the water intrusion volume, m³; $G_i$ is the gas reservoir reserve, m³; $B_i$ is natural gas volume coefficient under initial formation conditions; $Z_i$ is the initial formation natural gas deviation factor; $T_i$ is the initial formation temperature, K; $S_w$ is the water saturation; M is the water body multiplier; $R_{CO_2}$ is the $CO_2$ solubility in formation water, m³/m³.

In a specific embodiment, the proportion of different gas components in the reservoir pore space is calculated, the proportion of $CH_4$ in the reservoir pore space is calculated by substituting the following equation into the $H_2$—$CO_2$—$CH_4$ multi-component material balance equation:

$$V_H = bV \qquad (12)$$

$$V_{H\_dis} = \left[\frac{bVS_w}{(1-S_w)B_w}\right]R_H \qquad (13)$$

$$V_{dep} = V_i[1 - c_{eff}(p_i - p_{dep})] + V_{w\_p}B_{w\_dep} - W_{e\_dep} \qquad (14)$$

$$V_{dep\_dis} = \left[\frac{V_i(S_w + M)}{(1-S_w)B_{wi}} - V_{w\_p}\right]R_{H\_dep} \qquad (15)$$

Where, b is the proportion of natural gas occupying the gas-bearing pore space excluding the water intrusion volume; $V_{dep}$ is the gas-bearing pore space in the formation under depleted formation conditions, m³; $B_{w\_dep}$ is the formation water volume coefficient in the depleted formation condition; $W_{e\_dep}$ is the water intrusion volume in the depleted formation condition, m³; $R_H$, and $R_{H\_dep}$ are the solubility of natural gas under formation conditions and the solubility of natural gas under depleted formation conditions.

In a specific embodiment, when the proportion of different gas components in the reservoir pore space is calculated, the proportion of $H_2$ in the reservoir pore space is calculated by substituting the following equation into the $H_2$—$CO_2$—$CH_4$ multi-component material balance equation:

$$V_{H_2} = (1 - a - b)V \qquad (16)$$

$$V_{H_2\_dis} = \left[\frac{(1-a-b)VS_w}{(1-S_w)B_w}\right]R_{H_2} \qquad (17)$$

Where, $R_{H_2}$ is the solubility of $H_2$ under formation conditions, m³/m³:

The calculated $V_{H_2\_inj}$ value is the UHS capacity of the target depleted gas reservoir.

In a specific embodiment, the method for evaluating the UHS capacity in porous media of depleted gas reservoirs using $CO_2$ as cushion gas also comprises simulating hydrogen injection into a hydrogen storage by using a high-pressure and high-temperature device. And it is be used to verify the accuracy of $H_2$—$CO_2$—$CH_4$ multi-component material balance equation.

Figure 3:
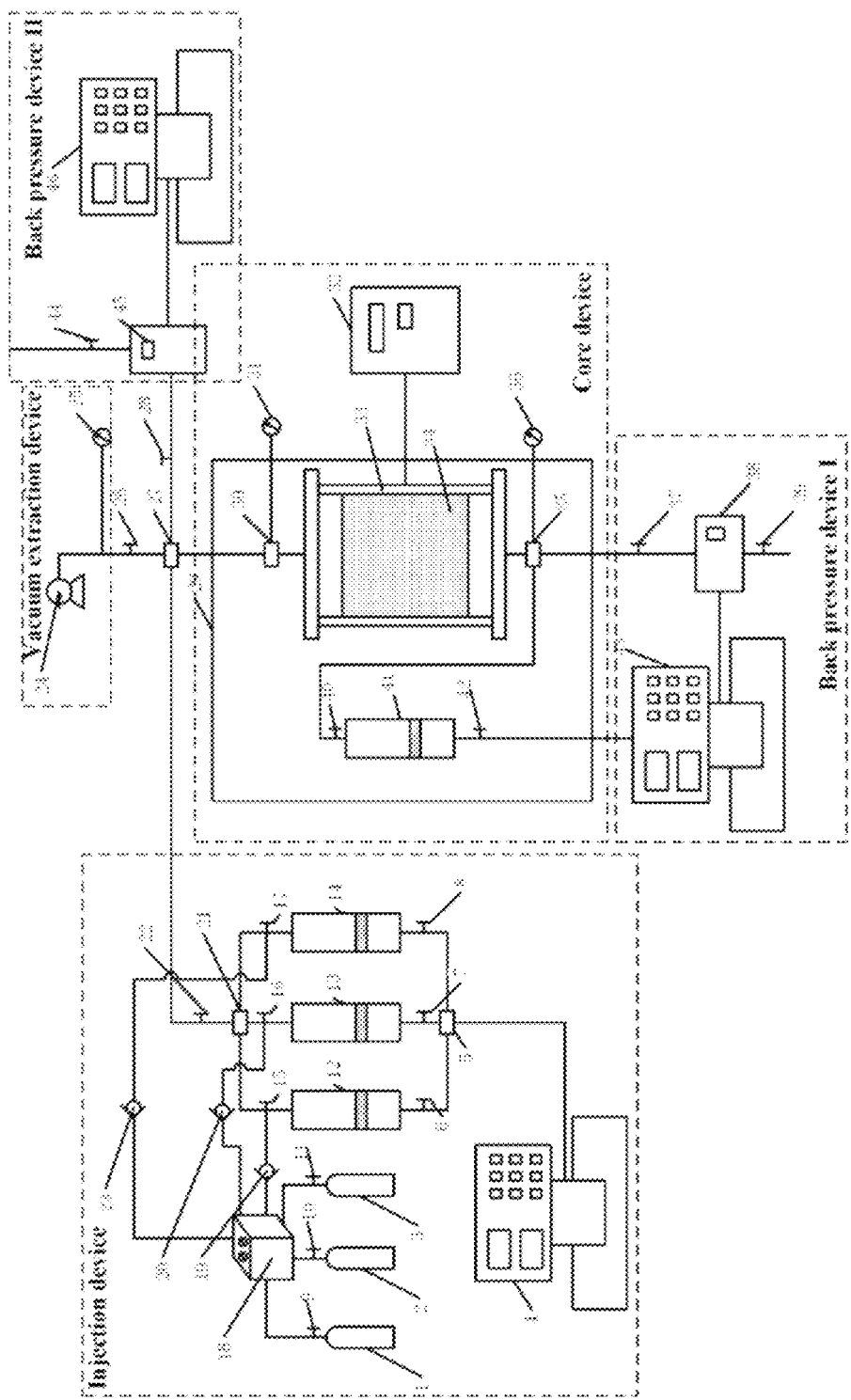
FIG. 3 is a schematic diagram of the structure of the high-temperature and high-pressure device in a specific embodiment.

In a specific embodiment, as shown in FIG. 3, the high pressure and high temperature device comprises an injection device, a core device, a back-pressure device I, a back-pressure device II, and a vacuum extraction device;

The injection device comprises a gas cylinder, a compressor (18), a gas intermediate vessel and a pressure pump I (4) connected in sequence. The gas intermediate vessel is further connected to the input end of the core device. The gas cylinder comprises an $H_2$ gas cylinder (1), a $CO_2$ gas cylinder (2) and a $CH_4$ gas cylinder (3) arranged in parallel. And the gas intermediate vessel comprises an $H_2$ intermediate vessel (12), a $CO_2$ intermediate vessel (13) and a $CH_4$ intermediate vessel (14);

The core device comprises a core holder (33) arranged in an oven (29), a confining pressure pump (32) and a formation water intermediate vessel (41). The core holder (33) is used for holding the core (34). The back-pressure device I comprises a pressure pump II (43) and a back-pressure valve I (38). The core holder (33) is provided with a pressure gauge I (31) and a pressure gauge II (36) respectively at the left and right ends. The confining pressure pump (32) is connected to the core holder (33). The output end of the core holder (33) is connected to the formation water intermediate vessel (41), and the other end of the formation water intermediate vessel (41) is connected to the pressure pump II (43). The pressure pump II (43) is connected to the output end of the core holder (33) via the back-pressure valve I (38);

The buck-pressure device II comprises a pressure pump III (46) and a back-pressure valve II (45), and the other end of the back-pressure valve II (45) is connected to the input end of the core holder (33);

The vacuum extraction device comprises an evacuator (24) and a pressure gauge III (25). The evacuator (24) is connected to the input end of the core holder (33), and the pressure gauge III (25) is provided on the connected line;

A valve is provided between sub-components, and a one-way valve I (19). A one-way valve II (20) and a one-way valve III (23) for flowing from the gas cylinder to the gas intermediate vessel is further provided between the $H_2$ gas cylinder (1) and the $H_2$ intermediate vessel (12), between the $CO_2$ gas cylinder (2) and the $CO_2$ intermediate vessel (13), and between the $CH_4$ gas cylinder (3) and the $CH_4$ intermediate vessel (14).

In a specific embodiment, the pressure pump I (4) is connected to the gas intermediate vessel by a four-way valve I (5), and the valves between the four-way valve I (5) and the $H_2$ intermediate vessel (12). $CO_2$ intermediate vessel (13) and $CH_4$ intermediate vessel (14) are labeled as valve I (6), valve II (7), and valve III (8), respectively. The valves between the $H_2$ gas cylinder (1), $CO_2$ gas cylinder (2) and $CH_4$ gas cylinder (3) and the compressor (18) are labeled as valve IV (9), valve V (10), valve VI (11), respectively. The valves between the one-way valve I (19), one-way valve II (20), one-way valve III (23) and the $H_2$ intermediate vessel (12). $CO_2$ intermediate vessel (13) and $CH_4$ intermediate vessel (14) are labeled as valve VII (15), valve VII (16), valve IX (17), respectively. The gas intermediate vessel and the core holder are connected by the four-way valve II (21) and the four-way valve III (27) respectively, and the other two lines of the four-way valve III (27) are connected to the evacuation device and the back-pressure device II respectively. The valve between the four-way valve II (21) and the four-way valve III (27) is labeled as valve X (22). The valve between the evacuator (24) and the four-way valve III (27) is labeled as valve XI (26). The valve between the back-pressure valve II (45) and the four-way valve III (27) is labeled as valve XII (28) The four-way valve III (27) is connected to the core holder (33) by a three-way valve (30), and the other end of the three-way valve (30) is connected to the pressure gauge I (31) The core holder (33) is connected to the formation water intermediate vessel 41) and the back-pressure valve I (38) by a four-way valve IV (35). The valve between the back-pressure valve I (38) and the four-way valve IV (35) is labeled as valve XIII (37), and the valve on the line connecting the back-pressure valve I (38) to air is labeled as valve XIV (39). The valves provided at the ends of the formation water intermediate vessel (41) are labeled as valve XV (40) and valve XVI (42) and the valve on the line connecting the back-pressure valve II (45) to air is labeled as valve XVII (44).

The specific use of the high-pressure and high-temperature device of the above embodiment to simulate the UHS injection comprises the following steps:

(1) Prepare the core (34), conduct experimental tests of compression coefficient on the core (34), wash and dry the core (34), and measure the dry weight, length, diameter, and porosity of the dried core (34); the results are shown in Table 1:

TABLE 1

Basic Parameters of the Core

| Core number | Rock compression coefficient/MPa$^{-1}$ | Length/ cm | Diameter/ cm | Porosity/ % |
|---|---|---|---|---|
| 1 | 0.00048 | 20 | 10 | 18.5 |

(2) Place the core 34 into the core holder 33, and then evacuate the entire device by the evacuation device;

(3) Load the confining pressure using the core device, inject the formation water into the core holder (33), in this embodiment, the mineralization of the target formation water is 10,000 mg/L, when injecting formation water, saturate the core with simulated formation water of the same mineralization, use the oven (29) to raise the temperature of the core holder (33) to simulated formation temperature and keep the temperature constant, and record the pump-in volume and the water output at the outlet end;

(4) Continuously inject $CH_4$ gas into the core (34) in the core holder (33) by the injection device, and measure the water output at the outlet end of the back-pressure device I to reach the simulated water saturation, and in this embodiment, the simulated water saturation is 42%;

(5) Close the outlet end of the back-pressure device I, continuously and slowly inject $CH_4$ gas into the core (34) in the core holder (33) by the injection device, connect the formation water intermediate vessel (41) with a water volume of 290 mL, which is equivalent to the water multiple of 1, and pressurize to reach the original formation pressure;

(6) Use the back-pressure device II for production, measure the output gas and water, and the pressure of the core holder (33) reaches the depleted formation pressure;

(7) After the system pressure is stabilized, inject $CO_2$ into the core (34) in the core holder (33) by the injection device, calculate the injected $CO_2$ volume using the equation of state through the flow difference shown in the pressure pump I (4), and record the stabilized formation pressure at different $CO_2$ injection volumes.

(8) After the pressure stabilization of the injected $CO_2$, inject $H_2$ into the core (34) in the core holder (33) by the injection device, calculate the injected $H_2$ volume using the equation of state through the flow difference shown in the pressure pump I (4), and record the stabilized formation pressure at different $H_2$ injection volumes.

In this embodiment, the production parameters of the cores are shown in Table 2:

TABLE 2

Production Parameters of the Core

| Core number | Original formation pressure/ MPa | Formation temperature/ °C. | Depleted formation pressure/ MPa | Gas production/ mL | Water production/ mL |
|---|---|---|---|---|---|
| 1 | 28 | 65 | 10 | 25320 | 5.2 |

Figure 4:
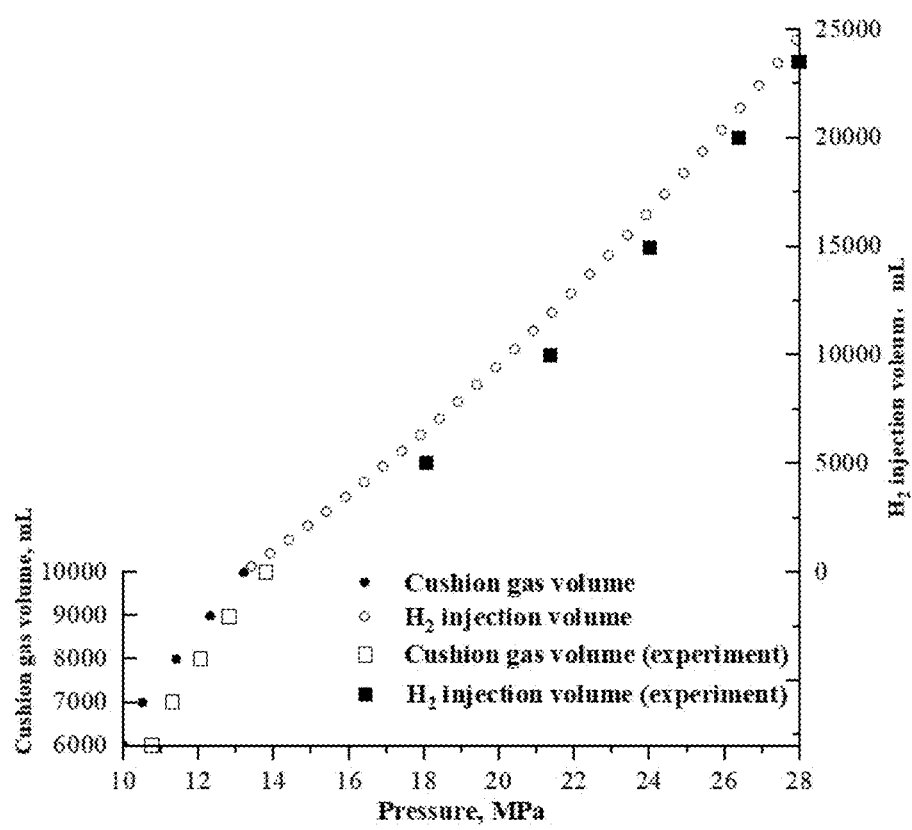
FIG. 4 is a schematic diagram of the simulation results of the UHS injection using cores in a specific embodiment.

The experiment results are shown in FIG. 4. The core pressure is recorded once every 1,000 mL of $CO_2$ injection after the core pressure is stabilized, and the total $CO_2$ injection volume is 10,000 mL. The core pressure is recorded for every 5,000 mL increase of $H_2$ injection after the core pressure is stabilized until the initial formation pressure is reached, and the final $H_2$ injection volume is 23,380 mL. The final $H_2$ injection volume obtained by using the $H_2$—$CO_2$—$CH_4$ multi-component material balance equation described in the present invention is 24,734 mL. The error is about 5.4%, which is within the acceptable range, proving the accuracy of the $H_2$l-$CO_2$—$CH_4$ multi-component material balance equation described in the present invention.

In a specific embodiment, a method for evaluating the UHS capacity in porous media of depleted gas reservoirs using $CO_2$ as cushion gas is used to evaluate the capacity of a target UHS. The basic parameters of the target UHS are shown in Table 3:

TABLE 3

Basic Parameters of the Target Gas Reservoir

| Parameter | Value | Parameter | Value |
|---|---|---|---|
| $G_i$ | 37000 × 10$^4$ [m$^3$] | $p_{dep}$ | 6 [MPa] |
| $p_i$ | 37 [MPa] | $V_{w\_p}$ | 84300 [m$^3$] |
| M | 10 | $T_i$ | 353.15[K] |
| T | 353.15[K] | $T_{dep}$ | 353.15[K] |
| $c_f$ | 0.00092 [MPa$^{-1}$] | $p_{sc}$ | 0.101325 [MPa] |
| $c_w$ | 0.000455 [MPa$^{-1}$] | $T_{sc}$ | 293.15[K] |
| $s_w$ | 0.45 | $Z_{sc}$ | 1 |
| m | 10 [g/L] | $W_{e\_dep}$ | 146166[m$^3$] |
| $\sigma_H$ | 70 [MPa] | $V_{CO2\_inj}$ | 1500 × 10$^4$ [m$^3$] |
| c | 10 [MPa] | $\sigma_h$ | 45 [MPa] |
| α | 43 [°] | φ | 11 [°] |

Figure 5:
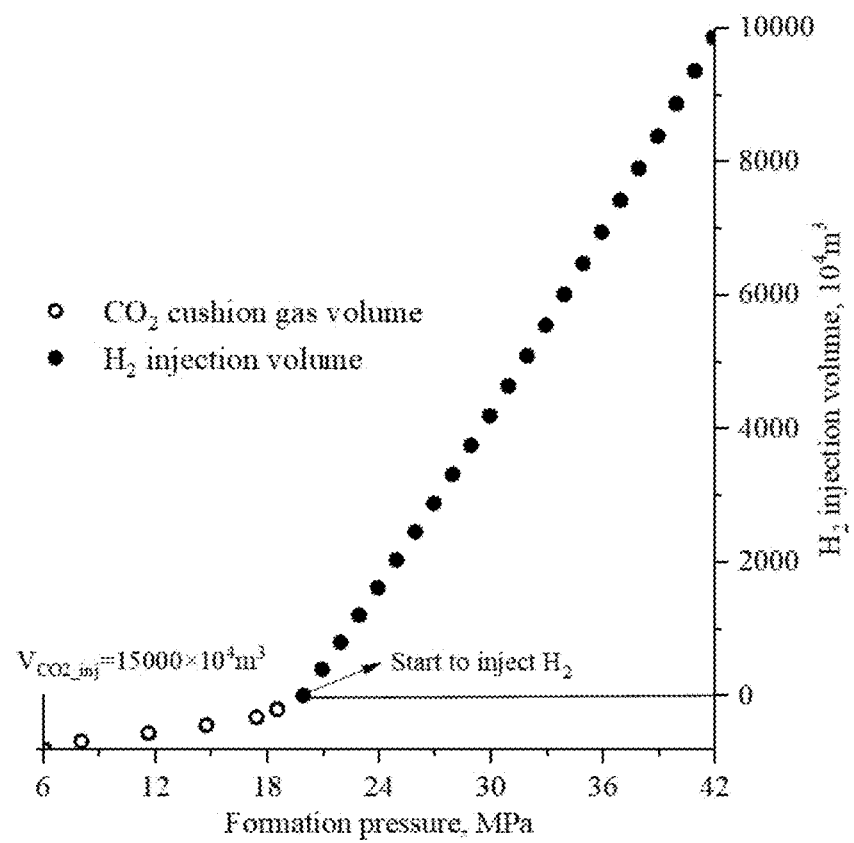
FIG. 5 is a schematic diagram of $H_2$ injection at a certain $CO_2$ cushion gas volume and the variation of formation pressure in a specific embodiment.

As shown in FIG. 5, the UHS capacity using $CO_2$ as cushion gas is evaluated by using existing data, and the $CO_2$ cushion gas volume is 15000×10$^4$ m$^3$. The safe formation pressure can reach 42 MPa by a comparative calculation with equation (1) and equation (2), and the $H_2$ injection volume at this time is 9916×10$^4$ m$^3$, i.e., the capacity of the target UHS is 9916×10$^4$ m$^3$.

In summary, the present invention can accurately evaluate the capacity of the UHS using $CO_2$ as cushion gas. Compared with the prior art, the present invention has significant improvements.

The above are only the preferred embodiments, which are not intended to limit the present invention in any form. Although the present invention has been disclosed as above with preferred embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. A method for evaluating the underground hydrogen storage (UHS) capacity in porous media of depleted gas reservoirs using $CO_2$ as cushion gas, comprising the following steps:
    S1: obtaining physical parameters required for UHS capacity evaluation based on geological and production data of the target depleted gas reservoir, wherein the physical parameters include original geological reserves, water saturation, water multiple, temperature of depleted gas reservoir, pressure of depleted gas reservoir, formation water intrusion under depleted formation conditions, accumulated water production, gas component, formation water mineralization;

S2: calculating the cap-rock breakthrough pressure and fault-slip pressure of the UHS based on the cap and fault properties of the target depleted gas reservoir to further estimate the highest operating pressure of the UHS;

S3: developing the $H_2$—$CO_2$—$CH_4$ multi-component material balance equation in underground porous media by considering the dissolution of three components of hydrogen, carbon dioxide and methane in formation water, and using the molar weight material balance method, and simulating the UHS injection with a high pressure and high temperature device to verify the accuracy of the $H_2$—$CO_2$—$CH_4$ multi-component material balance equation, wherein the $H_2$—$CO_2$—$CH_4$ multi-component material balance equation is:

$$\frac{p_{sc}V_{CO2\_inj}}{Z_{sc}RT_{sc}} = \frac{pV_{CO_2}}{Z_{CO_2}RT} + \frac{p_{sc}V_{CO2\_dis}}{Z_{sc}RT_{sc}} \quad (5)$$

$$\frac{p_{dep}V_{H\_dep}}{Z_{H\_dep}RT_{dep}} + \frac{p_{sc}V_{dep\_dis}}{Z_{sc}RT_{sc}} = \frac{pV_H}{Z_H RT} + \frac{p_{sc}V_{H\_dis}}{Z_{sc}RT_{sc}} \quad (6)$$

$$\frac{p_{sc}V_{H2\_inj}}{Z_{sc}RT_{sc}} = \frac{pV_{H_2}}{Z_{H_2}RT} + \frac{p_{sc}V_{H2\_dis}}{Z_{sc}RT_{sc}} \quad (7)$$

where, $p_{sc}$, $p$ and $p_{dep}$ are the standard condition pressure, formation pressure, and depleted formation pressure respectively, MPa; $V_{CO2\_inj}$, $V_{CO2}$ and $V_{CO2\_dis}$ are the volume of injected $CO_2$, the volume of $CO_2$ in the formation pore, and the volume of dissolved $CO_2$, respectively, m³; $Z_{sc}$, $Z_{CO2}$, $Z_{H\_dep}$, $Z_H$ and $Z_{H2}$ are the gas deviation factor under standard conditions, $CO_2$ deviation factor, natural gas deviation factor under depleted formation conditions, natural gas deviation factor under formation conditions, and $H_2$ deviation factor respectively; R is the ideal gas constant, 0.00831451 J·mol⁻¹·k⁻¹; $T_{sc}$, T and $T_{dep}$ are the standard condition temperature, formation temperature, and temperature of depleted gas reservoir respectively, K; $V_{H\_dep}$, $V_{dep\_dis}$, $V_H$ and $V_{H\_dis}$ are the volume of natural gas in the depleted gas reservoir formation, the volume of natural gas dissolved in the depleted gas reservoir formation, the volume of natural gas in the gas reservoir formation, and the volume of natural gas dissolved in the formation respectively, m³; $V_{H2\_inj}$, $V_{H2}$ and $V_{H2\_dis}$ are the volume of injected $H_2$, the volume of $H_2$ in the formation, and the volume of dissolved $H_2$ in the formation respectively, m³;

S4: substituting the parameters obtained from S1 and S2 into the $H_2$—$CO_2$—$CH_4$ multi-component material balance equation to calculate the proportion of different gas components in the pore space to finally determine the UHS capacity of the target depleted gas reservoir.

2. The method for evaluating the UHS capacity in porous media of depleted gas reservoirs using $CO_2$ as cushion gas according to claim 1, wherein in S2, the cap-rock breakthrough pressure is calculated by the following equation:

$$\chi = 1 - \frac{(\sigma_1 - \sigma_3)/2}{c\cos\phi + (\sigma_1 + \sigma_3)\sin\phi/2} = 1 - \frac{\tau_m}{\tau_m^*} \quad (1)$$

where, $\chi$ is the cap safety factor; when $\chi=0$, the shear failure occurs; $\sigma_1$ is the maximum effective principal stress, MPa; $\sigma_3$ is the minimum effective principal stress, MPa; c is the cohesion force, MPa; $\phi$ is the internal friction angle, °; $\tau_m$ is the maximum shear stress at a certain stress state, MPa; $\tau_m^*$ is the critical shear stress when the shear failure occurs, MPa.

3. The method for evaluating the UHS capacity in porous media of depleted gas reservoirs using $CO_2$ as cushion gas according to claim 1, wherein in S2, the fault-slip pressure is calculated by the following equation:

$$ST = \frac{\tau_s}{\sigma_n} \quad (2)$$

$$\sigma = \frac{\sigma_H + \sigma_h}{2} + \frac{\sigma_H - \sigma_h}{2}\cos 2\alpha \quad (3)$$

$$\tau = \frac{\sigma_H - \sigma_h}{2}\sin 2\alpha \quad (4)$$

where, ST is the fault slip trend index; when ST<0.6, the fault is mechanically stable; when ST≥0.6, the fault is at risk of slip; the larger the ST, the higher the risk of slip; $\tau$ and $\tau_s$ are the fault shear stress and the shear stress along the fault plane under a certain stress state respectively, MPa; $\sigma$ and $\sigma_n$ are the positive stress perpendicular to the fault plane and the effective positive stress respectively, MPa; $\sigma_H$ and $\sigma_h$ are the maximum principal stress and the minimum principal stress respectively, MPa; $\alpha$ is the dip angle of the fault plane, °.

4. The method for evaluating the UHS capacity in porous media of depleted gas reservoirs using $CO_2$ as cushion gas according to claim 1, wherein in S2, the highest operating pressure of the UHS is determined: The cap-rock breakthrough pressure and the fault-slip pressure are compared, and the smaller one is the highest operating pressure of the UHS.

5. The method for evaluating the UHS capacity in porous media of depleted gas reservoirs using $CO_2$ as cushion gas according to claim 1, wherein the high pressure and high temperature device comprises an injection device, a core device, a back-pressure device I, a back-pressure device II, and a vacuum extraction device;

the injection device comprises a gas cylinder, a compressor, a gas intermediate vessel and a pressure pump I connected in sequence; the gas intermediate vessel is further connected to the input end of the core device; the gas cylinder comprises an $H_2$ gas cylinder, a $CO_2$ gas cylinder and a $CH_4$ gas cylinder arranged in parallel, and the gas intermediate vessel comprises an $H_2$ intermediate vessel, a $CO_2$ intermediate vessel and a $CH_4$ intermediate vessel;

the core device comprises a core holder arranged in an oven, a confining pressure pump and a formation water intermediate vessel; the back-pressure device I comprises a pressure pump II and a back-pressure valve I; the core holder is provided with a pressure gauge I and a pressure gauge II respectively at the left and right ends; the confining pressure pump is connected to the core holder; the output end of the core holder is connected to the formation water intermediate vessel, and the other end of the formation water intermediate vessel is connected to the pressure pump II; the pressure pump II is connected to the output end of the core holder via the back-pressure valve I;

the back-pressure device II comprises a pressure pump III and a back-pressure valve II, and the other end of the back-pressure valve II is connected to the input end of the core holder;

the vacuum extraction device comprises an evacuator and a pressure gauge III; the evacuator is connected to the input end of the core holder, and the pressure gauge III is provided on the connected line;

a valve is provided between sub-components, and a one-way valve for flowing from the gas cylinder to the gas intermediate vessel is further provided between the $H_2$ gas cylinder and the $H_2$ intermediate vessel, between the $CO_2$ gas cylinder and the $CO_2$ intermediate vessel, and between the $CH_4$ gas cylinder and the $CH_4$ intermediate vessel.

6. The method for evaluating the UHS capacity in porous media of depleted gas reservoirs using $CO_2$ as cushion gas according to claim 1, wherein in S4, the proportion of different gas components in the reservoir pore space is calculated, and the proportion of $CO_2$ in the reservoir pore space is calculated by substituting the following equation into the $H_2$—$CO_2$—$CH_4$ multi-component material balance equation:

$$V_{CO_2} = aV \tag{8}$$

$$V = V_i[1 - c_{eff}(p_i - p)] + V_{w\_p}B_w - W_e \tag{9}$$

$$V_i = G_iB_i = G_i\left(\frac{p_{sc}}{Z_{sc}/T_{sc}}\right)\Big/\left(\frac{p_i}{Z_i/T_i}\right) \tag{10}$$

$$V_{CO_2\_dis} = \left[\frac{V_i(S_w + M)}{(1 - S_w)B_{wi}} - V_{w\_p} - \frac{aVS_w}{(1 - S_w)B_w}\right]R_{CO_2} \tag{11}$$

where, a is the proportion of $CO_2$ occupying the gas-bearing pore space of the formation excluding the water intrusion volume; V and $V_i$ are the gas-bearing pore space in the formation under different pressure conditions and the gas-bearing pore space in the formation under initial conditions, respectively, m³; $c_{eff}$ is the effective compression coefficient of the formation, MPa⁻¹; $p_i$ is the initial formation pressure, MPa; $V_{w\_p}$ is the water production volume, m³; $B_w$ and $B_{wi}$ are the formation water volume coefficient and the initial formation water volume coefficient, respectively; $W_e$ is the water intrusion volume, m³; $G_i$ is the gas reservoir reserve, m³; $B_i$ is natural gas volume coefficient under initial formation conditions; $Z_i$ is the initial formation natural gas deviation factor; $T_i$ is the initial formation temperature, K; $S_w$ is the water saturation; M is the water body multiplier; $R_{CO2}$ is the $CO_2$ solubility in formation water, m³/m³.

7. The method for evaluating the UHS capacity in porous media of depleted gas reservoirs using $CO_2$ as cushion gas according to claim 6, wherein in S4, the proportion of different gas components in the reservoir pore space is calculated, and the proportion of $CH_4$ in the reservoir pore space is calculated by substituting the following equation into the $H_2$—$CO_2$—$CH_4$ multi-component material balance equation:

$$V_H = bV \tag{12}$$

$$V_{H\_dis} = \left[\frac{bVS_w}{(1 - S_w)B_w}\right]R_H \tag{13}$$

$$V_{dep} = V_i[1 - c_{eff}(p_i - p_{dep})] + V_{w\_p}B_{w\_dep} - W_{e\_dep} \tag{14}$$

$$V_{dep\_dis} = \left[\frac{V_i(S_w + M)}{(1 - S_w)B_{wi}} - V_{w\_p}\right]R_{H\_dep} \tag{15}$$

where, b is the proportion of natural gas occupying the gas-bearing pore space excluding the water intrusion volume; $V_{dep}$ is the gas-bearing pore space in the formation under depleted formation conditions, m³; $B_{w\_dep}$ is the formation water volume coefficient in the depleted formation condition; $W_{e\_dep}$ is the water intrusion volume in the depleted formation condition, m³; $R_H$ and $R_{H\_dep}$ are the solubility of natural gas under formation conditions and the solubility of natural gas under depleted formation conditions.

8. The method for evaluating the UHS capacity in porous media of depleted gas reservoirs using $CO_2$ as cushion gas according to claim 7, wherein in S4, the proportion of different gas components in the reservoir pore space is calculated, and the proportion of $H_2$ in the reservoir pore space is calculated by substituting the following equation into the $H_2$—$CO_2$—$CH_4$ multi-component material balance equation:

$$V_{H_2} = (1 - a - b)V \tag{16}$$

$$V_{H_2\_dis} = \left[\frac{(1 - a - b)VS_w}{(1 - S_w)B_w}\right]R_{H_2} \tag{17}$$

where, $R_{H2}$ is the solubility of $H_2$ under formation conditions, m³/m³;

the calculated $V_{H2\_inj}$ value is the UHS capacity of the target depleted gas reservoir.

\* \* \* \* \*